(12) United States Patent
Pan et al.

(10) Patent No.: US 6,464,641 B1
(45) Date of Patent: Oct. 15, 2002

(54) METHOD AND APPARATUS FOR AUTOMATIC VESSEL TRACKING IN ULTRASOUND IMAGING

(75) Inventors: Lihong Pan, Brookfield, WI (US); Larry Y. L. Mo, Waukesha, WI (US); Michael J. Washburn, New Berlin, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 09/514,068

(22) Filed: Feb. 25, 2000

Related U.S. Application Data

(63) Continuation-in-part of application No. 09/201,982, filed on Dec. 1, 1998, now Pat. No. 6,068,598.

(51) Int. Cl.[7] .................................................. A61B 8/06
(52) U.S. Cl. ...................................... 600/453; 600/454
(58) Field of Search .......................... 600/437, 440–447, 600/450, 453, 454, 455–457, 407–436; 342/95, 120; 73/625, 626; 382/124, 128; 310/317, 334, 335

(56) References Cited

U.S. PATENT DOCUMENTS

| | | | | |
|---|---|---|---|---|
| 3,986,187 A | * | 10/1976 | Jacob | 342/95 |
| 4,630,612 A | * | 12/1986 | Uchida et al. | 600/437 |
| 5,280,787 A | * | 1/1994 | Wilson et al. | 600/456 |
| 5,297,552 A | * | 3/1994 | Mignot | 600/450 |
| 5,313,947 A | * | 5/1994 | Micco | 600/455 |
| 5,375,600 A | | 12/1994 | Melton et al. | 128/661.09 |
| 5,501,224 A | * | 3/1996 | Shiki | 600/456 |
| 5,690,116 A | | 11/1997 | Goujon | 128/661.08 |
| 5,785,655 A | * | 7/1998 | Goodsell, Jr. et al. | 600/441 |
| 5,800,356 A | * | 9/1998 | Criton et al. | 600/441 |
| 5,820,561 A | | 10/1998 | Olstad et al. | 600/453 |
| 5,941,826 A | | 8/1999 | Goujon | 600/451 |

FOREIGN PATENT DOCUMENTS

| | | |
|---|---|---|
| EP | 0842638 A2 | 5/1998 |
| EP | 1 005 834 A | 6/2000 |
| WO | 96 17549 A | 6/1996 |

\* cited by examiner

*Primary Examiner*—Marvin M. Lateef
*Assistant Examiner*—Ali M. Imam
(74) *Attorney, Agent, or Firm*—Ostrager Chong & Flaherty LLP

(57) ABSTRACT

Method and apparatus for automatically maintaining the range gate inside a moving blood vessel during ultrasound imaging. The range gate can be maintained at the vessel center, or at a certain distance from one of the vessel boundaries, or at a certain ratio of the respective distances from the two boundaries. The user first places the range gate on the blood flow being examined. An algorithm processes each successive image frame and automatically updates the information about vessel boundary positions and the vessel orientation angle in the vicinity of the range gate. If the range gate position relative to the vessel boundaries is different than that in the previous frame by more than a predetermined amount, the position of the range gate graphic and the orientation of the vessel slope cursor (and the Doppler angle) are automatically adjusted to the new values.

32 Claims, 5 Drawing Sheets

US 6,464,641 B1

METHOD AND APPARATUS FOR AUTOMATIC VESSEL TRACKING IN ULTRASOUND IMAGING

RELATED APPLICATION

This is a continuation-in-part of U.S. patent application Ser. No. 09/201,982 filed on Dec. 1, 1998, U.S. Pat. No. 6,068,598.

FIELD OF THE INVENTION

This invention generally relates to the imaging of moving ultrasound scatterers. In particular, the invention relates to methods for tracking the position and/or orientation of a blood vessel in medical diagnostic ultrasound imaging.

BACKGROUND OF THE INVENTION

Premium medical diagnostic ultrasound imaging systems require a comprehensive set of imaging modes. These are the major imaging modes used in clinical diagnosis and include timeline (spectral) Doppler, color flow Doppler, B mode and M mode. In the B mode, such ultrasound imaging systems create two-dimensional images of tissue in which the brightness of a pixel is based on the intensity of the returned echo. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. In the spectral Doppler imaging mode, the power spectrum of these Doppler frequency shifts are computed for visual display as velocity-time waveforms.

One of the primary advantages of Doppler ultrasound is that it can provide noninvasive and quantitative measurements of blood flow in vessels. Given the angle $\theta$ between the insonifying beam and the flow axis (hereinafter referred to as the "Doppler angle"), the magnitude of the velocity vector can be determined by the standard Doppler equation:

$$v = cf_d / (2f_0 \cos\theta)$$

where c is the speed of sound in blood, $f_0$ is the transmit frequency and $f_d$ is the motion-induced Doppler frequency shift in the backscattered ultrasound signal.

In conventional ultrasound scanners that perform B-mode and spectral Doppler imaging either simultaneously or in a segmented fashion, the angle between the Doppler beam cursor (beam centerline) and a vessel slope cursor in the B-mode image is used to convert Doppler frequency shifts into velocity units according to the Doppler equation. The operator is required to manually adjust (e.g., via a toggle switch) the vessel slope cursor based on the orientation of the vessel wall(s) in the B-mode image. The Doppler angle value is usually displayed along with the graphic. Since the Doppler angle adjustments are based on visual judgment, they are susceptible to error, especially if the angle step size is coarse. If fine angle adjustments are possible, the process can become time consuming.

An automatic method of adjusting the vessel slope cursor is taught in U.S. patent application Ser. No. 09/201,982, entitled "Method and Apparatus for Automatic Doppler Angle Estimation in Ultrasound Imaging". The Doppler angle is estimated automatically based on the B-mode and color flow (if available) image. The method uses an algorithm for automatic vessel slope measurement which first finds an optimal initial point within the sample volume or range gate, and then searches for the most reliable pixel points (near or far wall) based on a combination of intensity-only and intensity-difference thresholds, before performing a slope estimation. B-mode intensity data and, optionally, color flow velocity or power data (before gray/color mapping) are used. The algorithm may also be applied to methods for automatic tracking of vessel diameter and flow rate calculations.

In clinical ultrasound imaging studies, sometimes it is necessary to examine the blood flow at multiple sites along a segment of a blood vessel. With conventional scanners, if the vessel depth changes as the probe is moved along the vessel, the range gate needs to be maintained inside the vessel by manual control (e.g., using a trackball). When examining a flow at a pre-selected vessel position, the range gate can slide off of the vessel and may sometimes even shift outside the vessel due to tissue and/or probe motion.

Thus there is a need for a method by which the range gate can be automatically maintained inside a moving blood vessel being examined.

SUMMARY OF THE INVENTION

The present invention is directed to a method and an apparatus for automatically maintaining the range gate inside a moving blood vessel during ultrasound imaging. The range gate can be maintained at the vessel center, or at a certain distance from one of the vessel boundaries, or at a certain ratio of the respective distances from the two boundaries.

In accordance with the method of the preferred embodiment, the user first places the range gate on the blood flow being examined. Instead of pushing a control key or button to activate the automatic Doppler angle estimation based on a particular B-mode image frame (and color flow data if available), an algorithm processes each successive image frame and automatically updates the information about vessel boundary positions and the vessel orientation angle in the vicinity of the range gate. If the range gate position relative to the vessel boundaries is different than that in the previous frame by more than a predetermined amount, the position of the range gate graphic and the orientation of the vessel slope cursor (and the Doppler angle) are automatically adjusted to the new values. Optionally, the steering angle of the transmitted beam can also be automatically updated.

DETAILED DESCRIPTION OF THE PREFERRED EMBODIMENTS

Figure 1:
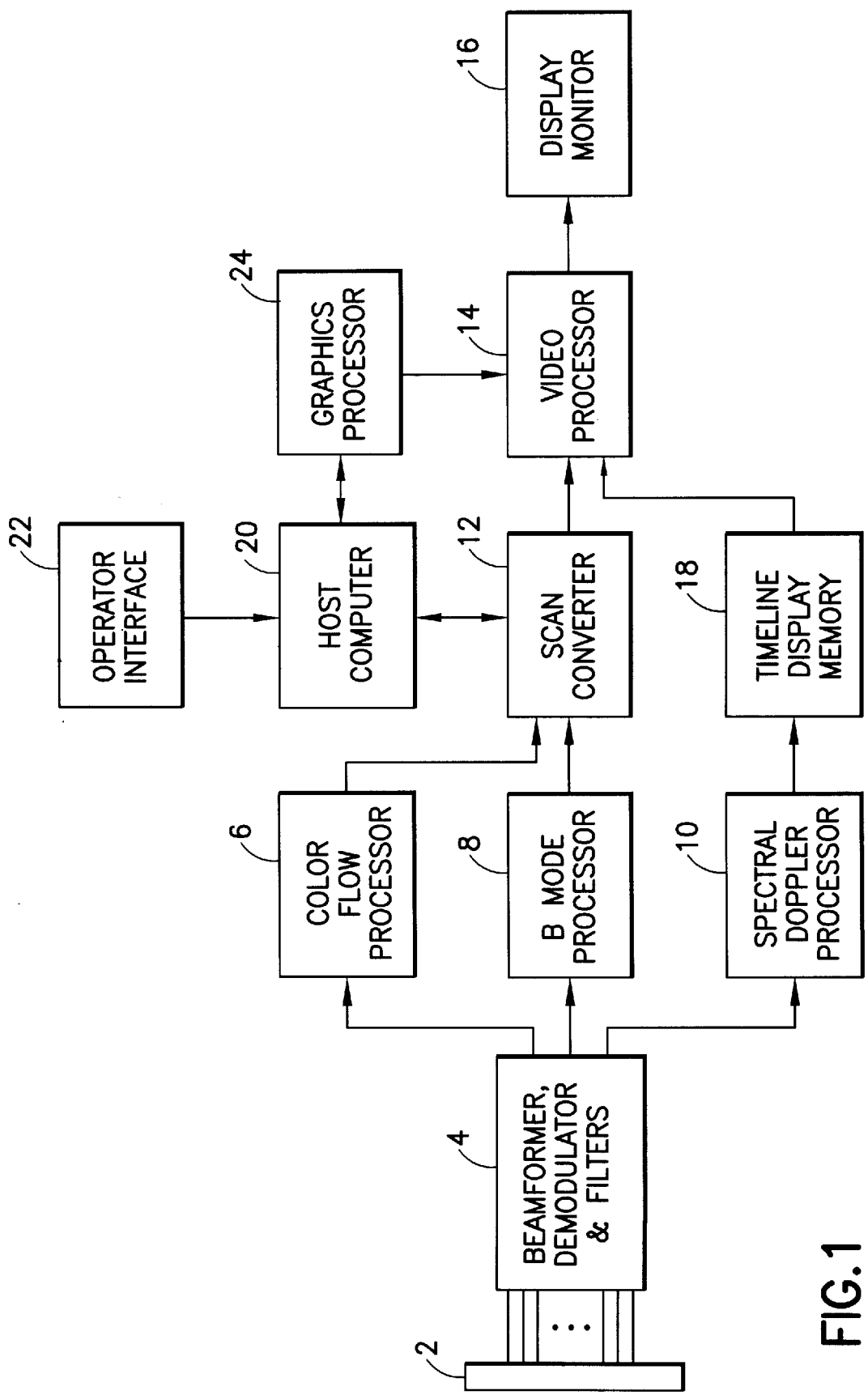
FIG. 1 is a schematic showing a block diagram showing the general architecture of an ultrasound imaging system which supports the preferred embodiments of the present invention.

One conventional ultrasound imaging system is generally depicted in FIG. 1. The main data path begins with the analog RF inputs to the beamformer board 4 from the transducer 2. The beamformer board 4 is responsible for the transmit and receive beamforming. The beamformer's signal inputs are the low-level analog RF signals from the transducer elements. The beamformer board 4, which comprises a beamformer, a demodulator and filters, outputs two summed digital baseband I (in-phase) and Q (quadrature) receive beams formed from acquired data samples. These data samples are derived from the reflected ultrasound from respective focal zones of the transmitted beams. The received data is sent to filters which are programmed with filter coefficients to pass a band of frequencies centered at the fundamental frequency $f_0$ of the transmit waveform or a (sub)harmonic frequency thereof.

The I/Q data output from the filters is sent to the midprocessor subsystem, where it is processed according to the acquisition mode and output as processed vector data. Typically, the midprocessor subsystem comprises a color flow processor 6, a B-mode processor 8 and a spectral Doppler processor 10. Alternatively, a digital signal processor or array of such processors can be programmed to process signals for all three modes.

The B-mode processor 8 converts the baseband I and Q data from the beamformer board 4 into a log-compressed version of the signal envelope. The B-mode function images the time-varying amplitude of the envelope of the signal as a gray scale. The envelope of a baseband signal is the magnitude of the vector which I and Q represent. The I,Q phase angle is not used in the B-mode display. The magnitude of the signal is the square root of the sum of the squares of the orthogonal components, i.e., $(I^2+Q^2)^{1/2}$. The B-mode intensity data is output to a B-mode acoustic line memory (not shown) in the scan converter 12.

The scan converter 12 accepts the processed B-mode vector data, interpolates where necessary, and converts the data into X-Y format for video display. The scan-converted frames are passed to a video processor 14, which maps the video data to a grayscale mapping for video display. A conventional ultrasound imaging system typically employs a variety of gray maps, which are simple transfer functions of the raw image data to display gray levels. The grayscale image frames are then sent to the display monitor 16 for display.

The B-mode images displayed by monitor 16 are produced from an image frame of data in which each datum indicates the intensity or brightness of a respective pixel in the display. An image frame may, e.g., comprise a 400×400 data array in which each intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a plane through the body being imaged.

The color flow processor 6 is used to provide a real-time two-dimensional image of blood velocity in the imaging plane. The frequency of sound waves reflecting from the inside of blood vessels, heart cavities, etc. is shifted in proportion to the velocity of the blood cells: positively shifted for cells moving towards the transducer and negatively for those moving away. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. The color flow processor 6 receives the summed left and right, complex I/Q data from the beamformer board 4 and processes it to calculate the mean blood velocity, variance (representing blood turbulence) and total prenormalization power for all sample volumes with in an operator-defined region. These three output values are then combined into two final outputs, one primary and one secondary. The primary output will be either velocity or power. The secondary output can be either variance or power. Which two values will be displayed is determined by the operator-selected display mode. Both values are sent to a color acoustic line memory (not shown) in the scan converter 12. The change or shift in backscattered frequency increases when blood flows toward the transducer and decreases when blood flows away from the transducer. Typically, color flow mode displays hundreds of adjacent sample volumes simultaneously, all laid over a B-mode image and color-coded to represent each sample volume's velocity.

In the color flow mode of the conventional ultrasound imaging system being described here, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilohertz range. A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by a beamformer.

For example, the traditional color firing sequence is a series of firings (e.g., tone bursts) along the same position, which firings produce the respective receive signals:

$$F_1 \, F_2 \, F_3 \, F_4 \ldots F_M$$

where $F_i$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point is filtered to produce the respective difference signals:

$$(F_1-F_2) \, (F_2-F_3) \, (F_3-F_4) \ldots (F_{M-1}-F_M)$$

and these differences are input to a color flow velocity estimator. Typically, the corner turner memory, wall filter and parameter (e.g., velocity) estimators are incorporated into the color flow processor 6.

The color and B-mode acoustic line memories in scan converter 12 respectively accept processed digital data from the color flow and B-mode processors. These components of the scan converter also perform the coordinate transformation of the color flow and B-mode data from polar coordinate (R-θ) sector format or Cartesian coordinate linear format to appropriately scaled Cartesian coordinate display pixel data, which is stored in an X-Y display memory (not shown) in the scan converter. Color flow images are produced by superimposing a color image of the velocity of moving material, such as blood, over a black and white anatomical B-mode image.

If the image to be displayed is a combination of one B-mode frame and one color flow frame, then both frames are passed to the video processor 14, which maps the B-mode data to a gray map and maps the color flow data to a color map for video display. In the final displayed image, the color pixel data is superimposed on the grayscale pixel data.

In spectral Doppler imaging, the I/Q components are integrated (summed) over a specific time interval and then sampled by the spectral Doppler processor 10. The summing interval and the transmit burst length together define the length of the sample volume as specified by the user. A "sum and dump" operation effectively yields the Doppler signal backscattered from the sample volume. The Doppler signal is passed through a wall filter which rejects any clutter in the signal corresponding to stationary or very slow-moving tissue. The filtered output is then fed into a spectrum analyzer, which typically takes Fast Fourier Transforms (FFTs) over a moving time window of 32 to 128 samples. Each FFT power spectrum is compressed and then output by the spectral Doppler processor 10 to a timeline display memory 18. The video processor 14 maps the compressed spectral Doppler data to a gray scale for display on the monitor 16 as a single spectral line at a particular time point in the Doppler velocity (frequency) versus time spectrogram.

System control is centered in a host computer 20, which accepts operator inputs through an operator interface 22 (e.g., a control panel) and in turn controls the various subsystems. The host computer 20 performs system level control functions. It accepts inputs from the operator via the operator interface 22 as well as system status changes (e.g., mode changes) and makes appropriate system changes. A system control bus (not shown) provides the interface from the host computer to the subsystems. A scan controller (not shown) provides real-time (acoustic vector rate) control inputs to the various subsystems. The scan controller is programmed by the host computer with the vector sequences and synchronization options for acoustic frame acquisitions. Thus, the scan controller controls the beam distribution and the beam density. The scan controller transmits the beam parameters defined by the host computer to the subsystems via a scan control bus (not shown).

The conventional system has the capability to superimpose graphical symbols on any ultrasound image. The superimposition of graphics on the image frame is accomplished in the video processor 14, which receives the ultrasound image frame from the X-Y display memory in the scan converter 12 and the graphics data from a graphics processor 24. The graphics processor generates data corresponding to graphical symbols to be displayed in the image frame, e.g., the range gate graphics, the Doppler beam cursor and the vessel slope cursor described in detail below, in response to instructions from the host computer 20. In the preferred embodiment, the vessel slope, Doppler angle and range gate position are computed in the host computer. The host computer then sends instructions to the graphics processor for generating graphics representing those positional parameters. Alternatively, the host computer may be programmed to generate the graphical data and then store that graphical data in a graphics display memory for subsequent transfer to the video processor.

Figure 5:
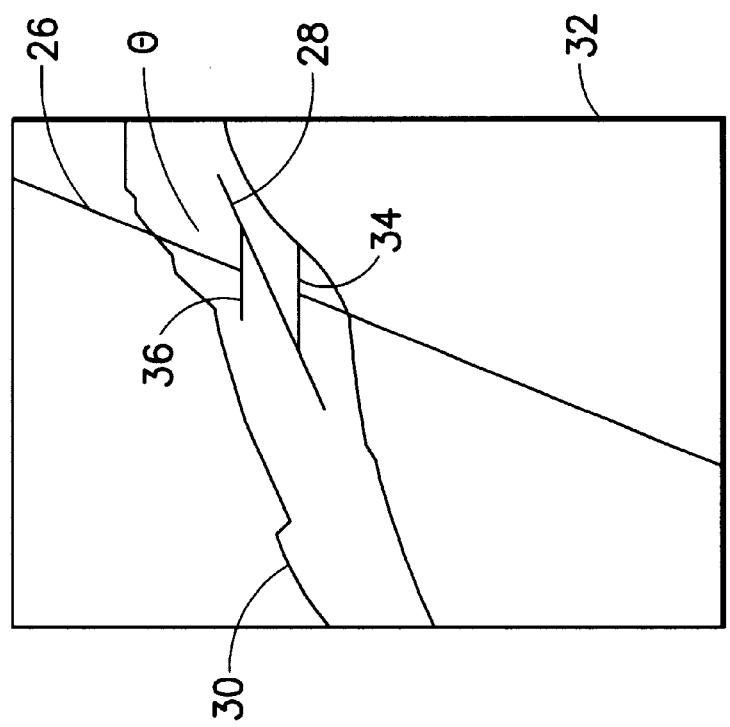
FIG. 5 is a schematic depicting the ultrasound image of FIG. 2 with a Doppler beam cursor and a vessel slope cursor superimposed thereon.

In the system depicted in FIG. 1, the Doppler angle is estimated automatically by the host computer 20. The estimated Doppler angle value is then used by the host computer to estimate the flow velocity as a function of the Doppler frequency shift. Referring to FIG. 5, the angle between a Doppler beam cursor (beam centerline) 26 and a vessel slope cursor 28 on a vessel 30 in the B-mode image 32 is used to convert Doppler frequency shifts into velocity units according to the Doppler equation. The Doppler angle value is usually displayed along with the graphic.

Figure 2:
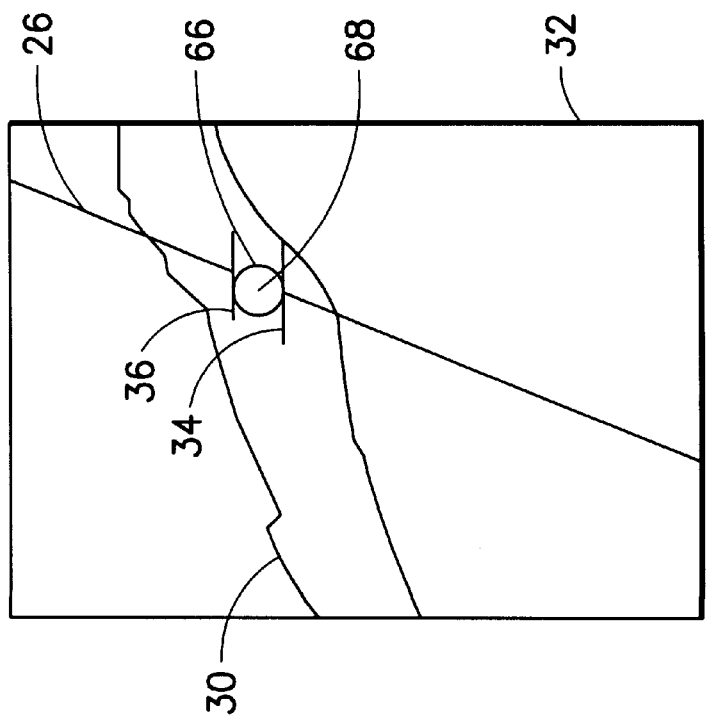
FIG. 2 is a schematic depicting an ultrasound image of a portion of a blood vessel with a Doppler beam cursor superimposed thereon.

To accomplish the foregoing, the user requests an automatic Doppler angle estimation by pressing a rotary knob on the operator interface 22 (see FIG. 1) after the user has placed the Doppler range gate (sample volume) graphic, consisting of a range gate top graphic 36 and a range gate bottom graphic 34, on the vessel 30 in the image 32, as seen in FIG. 2, also via the operator interface. The host computer 20 automatically reads the current frame of B-mode and color flow (if available) image data from the display memory in the scan converter 12 (or from a cine memory not shown) (step 40 in FIG. 7). Based on that image data, a Doppler angle is computed, and the Doppler angle value and graphic are updated. If the user is not satisfied with the automatically estimated Doppler angle, the user can adjust the vessel slope cursor by dialing the rotary knob that he pressed to initiate the automatic Doppler angle estimation.

Figure 7:
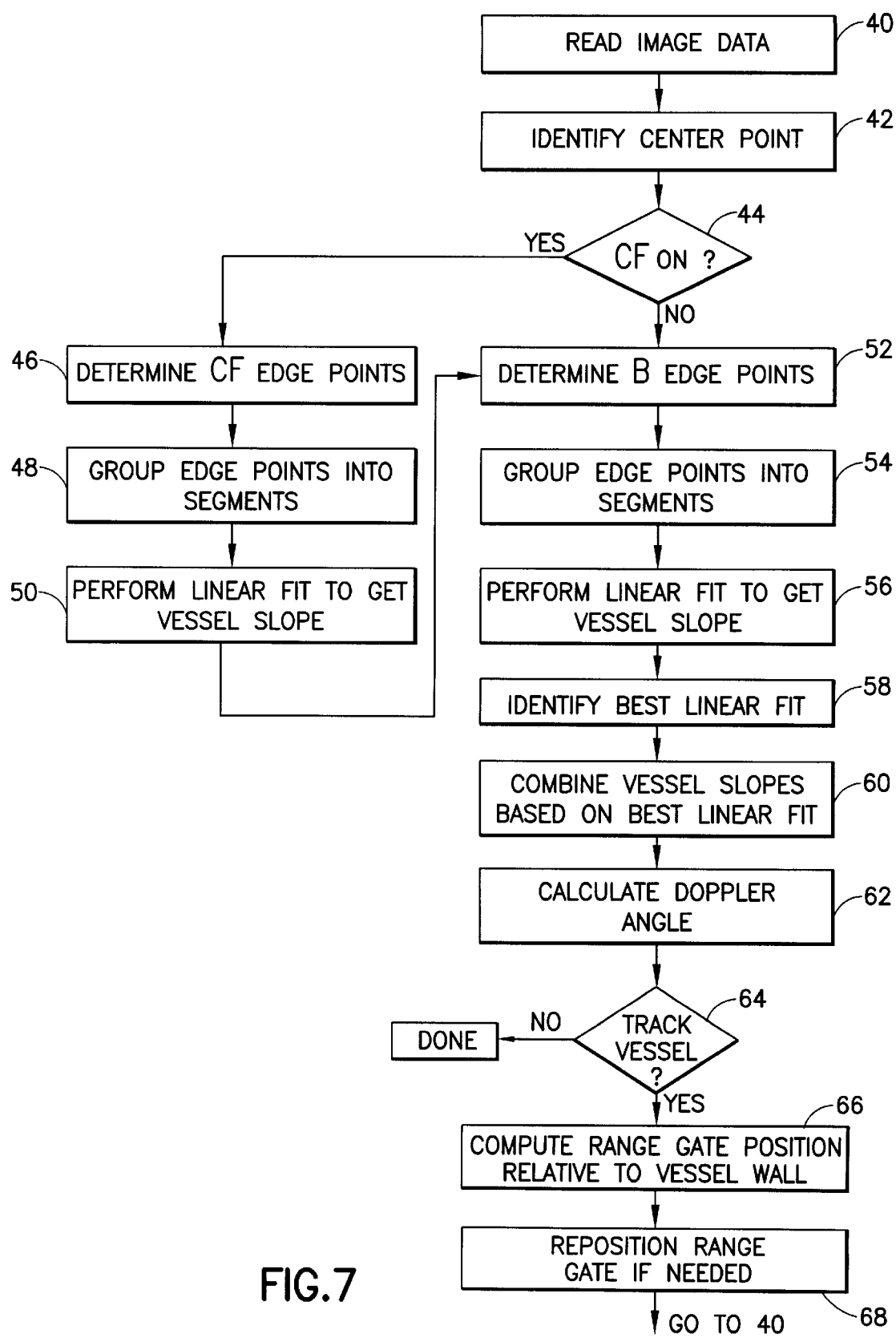
FIG. 7 is a flowchart depicting the algorithm for automatically adjusting the range gate position in accordance with the preferred embodiment of the invention.

To automatically compute a Doppler angle, the host computer performs the algorithm shown in FIG. 7 on the frame of image data read in step 40. A center point of a search area is identified in step 42 as follows. Referring to FIG. 2, if the average of a number of B-mode intensity values in a small area 66 about the center point 68 of the Doppler range gate is at or below some threshold, then that location is used as the center point of the searching algorithm. If the B-mode intensity values are above the threshold, then the host computer searches outward from that point by ½ of the total range gate width in all directions to determine the area with the minimum average B-mode intensity values (typical of scattering from blood). If that area of minimum average intensity is below the intensity at the original center point area by some percentage, then the center point is moved to the center 70 of this minimum area, as seen in FIG. 3.

Figure 3:
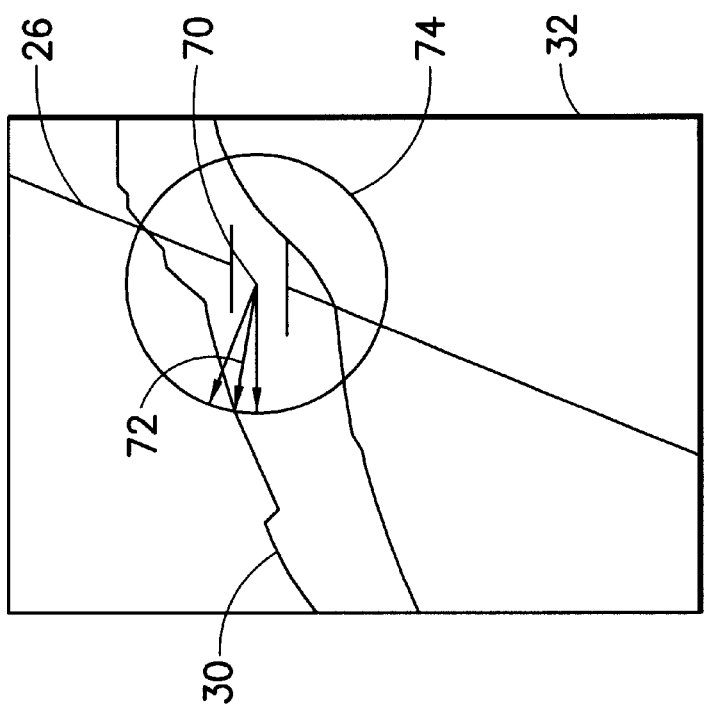
FIG. 3 is a schematic depicting the ultrasound image of FIG. 2 with edge point search information in accordance with the preferred embodiment of the invention superimposed thereon.

The host computer then determines (step 44 in FIG. 7) whether the image frame being processed includes color flow data at pixel addresses corresponding to the location of the center point 70 (see FIG. 3). If the image frame includes color flow data corresponding to the center point, then the host computer searches out from the center point 70 along radial lines 72 which are angularly spaced S degrees apart over an entire 360° range, as shown in FIG. 3. The distance to search from the center is D cm. This edge search area is indicated by circle 74 in FIG. 3.

Figure 4:
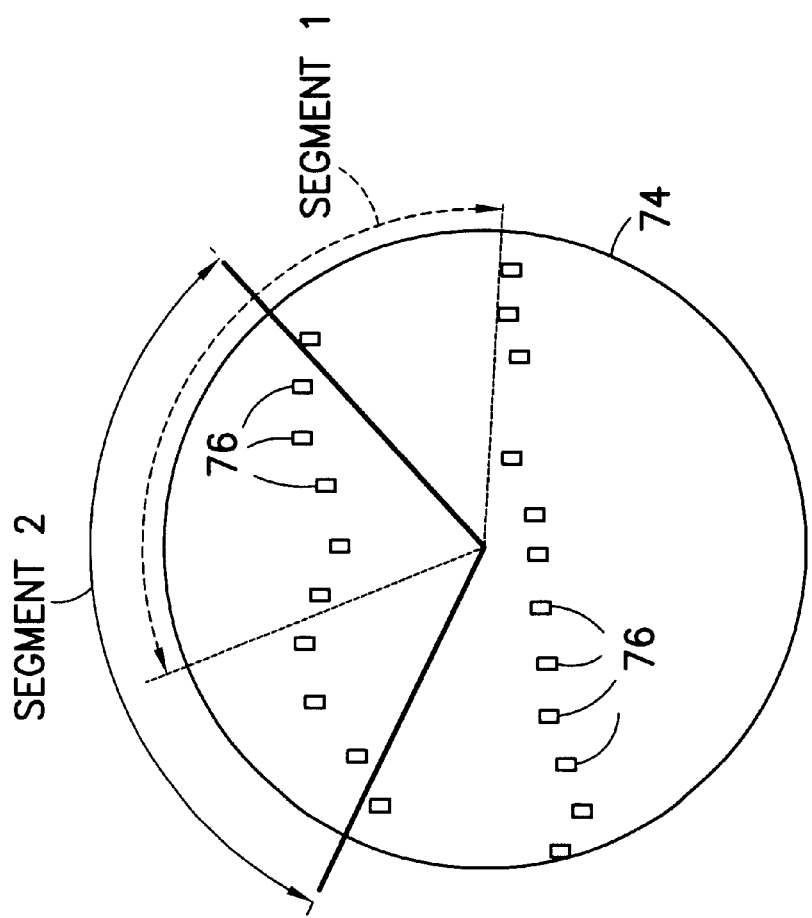
FIG. 4 is a schematic depicting segmentation of the edge points in accordance with the preferred embodiment of the invention.

Along each radial line 72, the host computer searches from the center point 70 and stores the point as an edge point if it is the first of X ($\geq 2$) points displaying B-mode intensity data instead of color flow velocity or power data (step 46 in FIG. 7). Exemplary edge points are depicted as rectangles 76 in FIG. 4. If no such point is found before searching D cm or finding the edge of the color region of interest, then no edge point is marked along that radial line. Once each radial line is searched, all the edge points 76 in a certain segment of the edge point search area (e.g., Segment 1 indicated by dotted lines in FIG. 4) are grouped together (step 48) and fed to a line-fit algorithm which generates both a vessel slope estimate and a goodness-of-fit measurement (step 50). This is repeated for other segments (e.g., Segment 2 indicated by solid straight lines in FIG. 4) and in each case the slope of the vessel and the goodness of fit are recorded. The segments may overlap each other by some number of degrees, as do Segments 1 and 2 shown in FIG. 4. If a particular segment does not have some minimum number of edge points within it, then that segment is disregarded.

In addition to the foregoing, the algorithm also determines B-mode edge points (step 52) by searching the B-mode intensity data from the center point in radial lines spaced S degrees apart over an entire 360° range. The distance to search from the center is D cm. Along each radial line, each B-mode intensity value (corresponding to respective pixels) is replaced with the average of itself and its two neighbors along the radius. The peak and minimum intensities along the averaged radial line as well as the largest difference (from one pixel to the next) are each recorded. If the difference between the peak and minimum intensities does not exceed some threshold, then no edge point is specified for this ray. If the difference between the peak and minimum intensities exceeds the threshold, then a search is started at some number of points from the center and stops when a point (the edge point) is found to exceed a difference-only threshold, an intensity-only threshold or a combined difference and intensity threshold. For example, if the pixel location is 50% of the maximum intensity and 30% of the maximum difference, then it would pass the combined difference and intensity threshold. The intensity at the edge point is noted. If no such point is found before searching D cm or finding the edge of the B-mode image, then no edge point is marked along that radial line. Once each radial line has been searched, some percent of the edge points are disregarded. The disregarded edge points are those associated with the lowest intensities. All of the remaining edge points in a certain segment of the edge point search area are grouped (step 54) and then fed to a line-fit algorithm which generates both a vessel slope estimate and a goodness-of-fit measurement (step 54). This is repeated for other segments, and in each case the vessel slope and the goodness of fit are recorded. The segments may overlap each other by some number of degrees. If a particular segment does not have some minimum number of edge points within it, then that segment is disregarded.

If no B-mode or color flow mode segment generated enough edge points to get a vessel slope estimate, the distance D is increased and the algorithm is rerun. (If rerunning the algorithm still results in no vessel slope estimates, then the Doppler angle remains unchanged.)

At this point in the algorithm, estimates of the vessel slope and their corresponding goodness-of-fit measurements are known for some number of segments (for B mode and possibly color flow mode). The segment having the best goodness of fit is identified (step 58) and its vessel slope is combined (averaged) with all the other vessel slope estimates that have a goodness of fit measurement not exceeding some difference relative to the best one (step 60). However, if color is active and the best color vessel slope exceeds some number of degrees (indicating a vessel somewhat vertical), then only color data is used in this vessel slope-combining algorithm. This is done because somewhat vertical vessel walls are difficult to detect in B-mode due to the lateral smearing of the image data. On the other hand, if color is not active, steps 46, 48 and 50 in FIG. 7 are not performed and step 60 combines only vessel slopes derived from B-mode edge points.

The host computer determines the Doppler angle by calculating (step 62 in FIG. 7) the angle between the combined vessel slope 28 and the Doppler beam cursor 26, as shown in FIG. 5. The host computer then uses the calculated Doppler angle value to compute the velocity in accordance with the Doppler equation.

Figure 6:
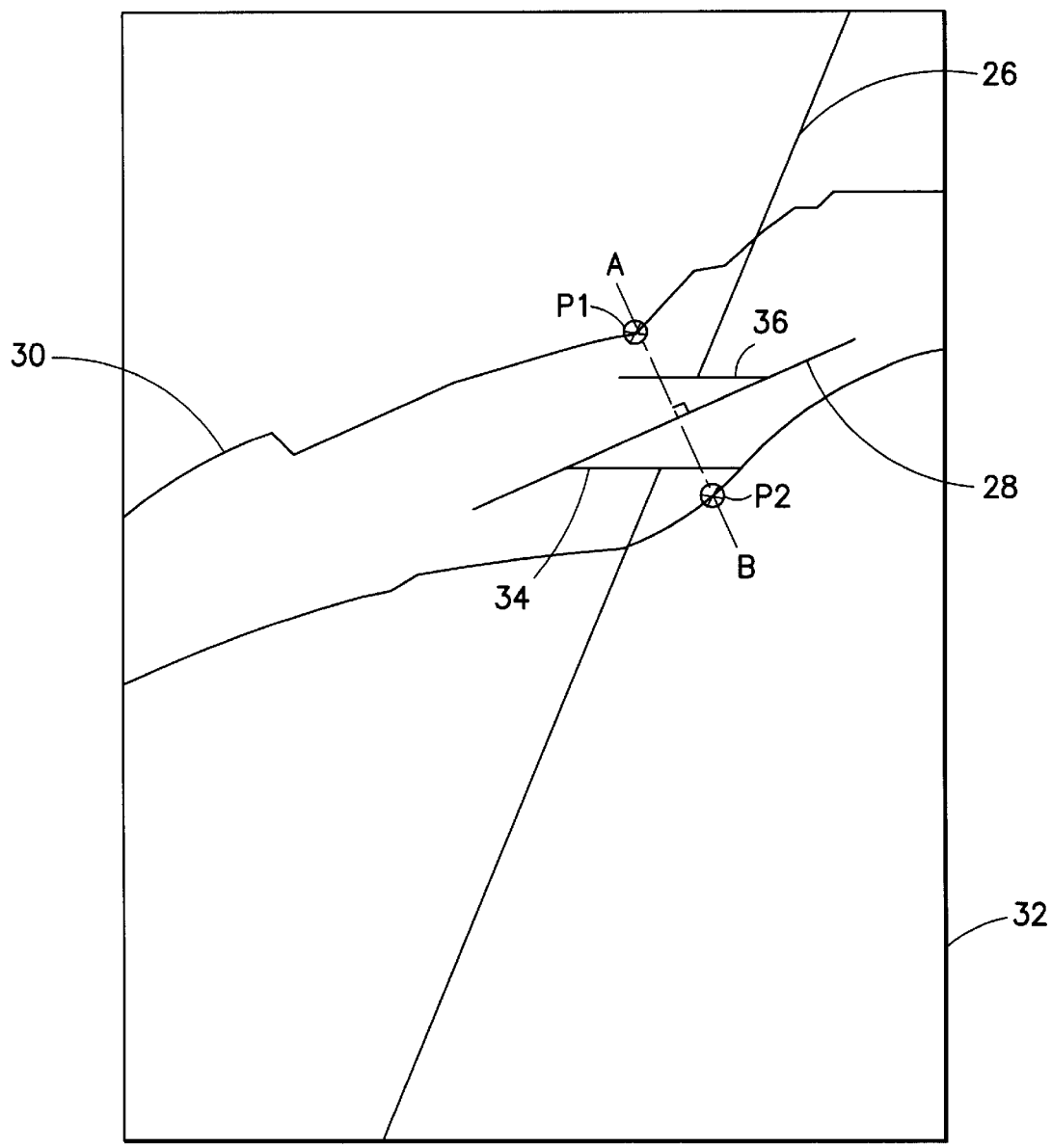
FIG. 6 is a schematic depicting the step of determining which pixels, along a line perpendicular to the vessel slope cursor, display the vessel wall.

In accordance with the preferred embodiment of the invention, the host computer also automatically adjusts the position of the range gate so that it is maintained inside a blood vessel during relative motion of the tissue and probe. A pushbutton can be provided on the operator interface to enable a system user to select this automatic vessel tracking option. After the Doppler angle is calculated, the host computer detects whether the automatic vessel tracking option has been selected (step 64) in FIG. 7. The first step 66 in the vessel tracking algorithm is to compute the current position of the range gate relative to the vessel wall. For example, the host computer can determine the locations of the pixels, in a direction perpendicular to the vessel wall orientation, which respectively correspond to the vessel wall boundaries. As shown in FIG. 6, the host computer determines the addresses of pixels P1 and P2 lying along line A–B and overlying respective vessel wall boundaries. The line A–B is perpendicular to the current vessel slope, which is indicated by the vessel slope cursor 28 in FIG. 6. This can be accomplished, for example, by searching the B-mode intensity data from the center point in opposite directions along the line A–B and determining the B-mode edge points as previously described for step 52 shown in FIG. 7 or using already obtained edge points. The orientation of line A–B is determined by the current Doppler angle information.

The addresses of the pixels used to display the range gate graphics are sent to the host computer by the graphics processor. The addresses of pixels P1 and P2 establish the position of the vessel relative to the range gate. If the host computer determines that the range gate position relative to the vessel boundaries is displaced from its position in the previous frame by greater than a predefined amount, the host computer instructs the graphics processor to move the range gate to a new position. The graphics processor then computes the pixel addresses for the newly adjusted position of the range gate graphic. The range gate position can be maintained at the center of the vessel, at a predetermined distance from one of the vessel boundaries or at a predetermined ratio from the two vessel boundaries. The algorithm then returns to step 40 in FIG. 7 and retrieves a new image frame. The Doppler angle will then be re-estimated and updated based on the new image frame. As long as the vessel tracking option is in the active state, the entire vessel tracking and angle update process will be repeated.

Although the preferred embodiment has been disclosed in the context of an ultrasound imaging system having a host computer and a graphics processor, the functions of both can be performed by one processor. In particular, the functions shown in the flowchart of FIG. 7 can be performed by a single processor. Furthermore, although FIG. 1 shows the architecture of a conventional ultrasound imaging system having multiple processes and a host computer, all of the data processing and computing functions could be performed by a single computer, e.g., a personal computer, having sufficient processing power.

While the invention has been described with reference to preferred embodiments, it will be understood by those skilled in the art that various changes may be made and equivalents may be substituted for elements thereof without departing from the scope of the invention. For example, although along each radial line each B-mode intensity value (corresponding to respective pixels) can be replaced with the average of itself and its two neighbors along the radius, any suitable smoothing filter which reduces statistical variations can be used. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A method comprising the steps of:
   (a) displaying an image of a blood vessel;
   (b) storing a frame of image parameter values from which said image was derived, said image parameter values corresponding to respective pixels in said image;
   (c) placing a graphic representing a range gate overlying said blood vessel in said image;
   (d) determining a vessel slope of the blood vessel at or near said range gate based on said frame of image parameter values;
   (e) placing a graphic representing said vessel slope overlying said blood vessel in said image;
   (f) determining the position of a boundary of the blood vessel; and
   (g) adjusting the position of said range gate if the change in the position of the boundary relative to said range gate is equal to or greater than a predetermined threshold.

2. The method as recited in claim 1, wherein said step (f) comprises the step of determining the address of a pixel on said boundary.

3. The method as recited in claim 2, wherein said pixel on said boundary is located along a line generally perpendicular to said vessel slope graphic.

4. The method as recited in claim 3, wherein said step (f) further comprises the step of searching for an edge point along said line generally perpendicular to said vessel slope graphic in accordance with a search algorithm.

5. The method as recited in claim 2, wherein said step (f) further comprises the step of searching for an edge point along a line in accordance with a search algorithm.

6. The method as recited in claim 5, wherein said search algorithm comprises the steps of:
   applying a smoothing filter to reduce statistical variations;
   storing the peak and minimum image parameter values and the largest difference between image parameter values corresponding to adjacent pixels;
   if a difference between said peak and minimum image parameter values exceeds a predetermined threshold, searching for a point along said line having an image parameter value which satisfies at least one of a difference criterion and a value criterion; and
   identifying said point as said edge point.

7. The method as recited in claim 5, wherein said image parameter values comprise B-mode intensity values for some of said pixels and color flow estimates for others of said pixels in said frame, and said step of searching for an edge point comprises the steps of:
   searching for a point which is the first of X points having B-mode intensity values instead of color flow estimates; and identifying said point as said edge point.

8. The method as recited in claim 1, wherein said step (g) comprises the step of displaying said range gate graphic at a predetermined position relative to said boundary.

9. The method as recited in claim 1, wherein said image parameter values comprise B-mode intensity values for at least some of said pixels.

10. A system comprising:
    a display device comprising a multiplicity of pixels;
    a memory for storing a frame of image parameter values from which said ultrasound image was derived, said image parameter values corresponding to respective pixels in said image;
    a computer programmed to perform the steps of:
    (a) controlling said display device to display an ultrasound image of a blood vessel with a graphic representing a range gate overlying said blood vessel;
    (b) determining a vessel slope of the blood vessel at or near said range gate based on said frame of image parameter values;
    (c) controlling said display device to place a graphic representing said vessel slope overlying said blood vessel in said image;
    (d) determining the position of a boundary of the blood vessel; and
    (e) controlling said display device to adjust the position of said range gate if the change in the position of the boundary relative to said range gate is equal to or greater than a predetermined threshold.

11. The system as recited in claim 10, wherein said step (d) comprises the step of determining the address of a pixel on said boundary.

12. The system as recited in claim 11, wherein said pixel on said boundary is located along a line generally perpendicular to said vessel slope graphic.

13. The system as recited in claim 11, wherein said step (d) further comprises the step of searching for an edge point along a line in accordance with a search algorithm.

14. The system as recited in claim 12, wherein said step (d) further comprises the step of searching for an edge point along said line generally perpendicular to said vessel slope graphic in accordance with a search algorithm.

15. The system as recited in claim 10, wherein said image parameter values comprise B-mode intensity values for at least some of said pixels.

16. The system as recited in claim 13, wherein said search algorithm comprises the steps of:
    applying a smoothing filter to reduce statistical variations;
    storing the peak and minimum image parameter values and the largest difference between image parameter values corresponding to adjacent pixels;
    if a difference between said peak and minimum image parameter values exceeds a predetermined threshold, searching for a point along said line having an image parameter value which satisfies at least one of a difference criterion and a value criterion; and
    identifying said point as said edge point.

17. The system as recited in claim 13, wherein said image parameter values comprise B-mode intensity values for some of said pixels and color flow estimates for others of said pixels in said frame, and said step of searching for an edge point comprises the steps of:
    searching for a point which is the first of X points having B-mode intensity values instead of color flow estimates; and
    identifying said point as said edge point.

18. The system as recited in claim 10, further comprising:
    an ultrasound transducer array comprising a multiplicity of transducer elements;
    a transmit beamformer for pulsing selected transducer elements to transmit a series of ultrasound transmit beams in a scan plane;

a receive beamformer coupled to selected transducer elements of said transducer array for acquiring respective receive signals subsequent to respective beam transmits;

a signal processor for forming vectors of image parameter values from said receive signals;

a scan converter for converting said vectors into a frame of image parameter values and storing said frame of image parameter values in said memory; and a video processor comprising a grayscale mapping for mapping said frame of image parameter values retrieved from said memory into grayscale pixel values.

19. A system comprising:

means for displaying an image of a blood vessel;

means for storing a frame of image parameter values from which said ultrasound image was derived, said image parameter values corresponding to respective pixels in said image;

means for placing a graphic representing a range gate overlying said blood vessel in said image;

means for determining a vessel slope of the blood vessel at or near said range gate based on said frame of image parameter values;

means for placing a graphic representing said vessel slope overlying said blood vessel in said image;

means for determining the position of a boundary of the blood vessel; and means for adjusting the position of said range gate if the change in the position of the boundary relative to said range gate is equal to or greater than a predetermined threshold.

20. A system comprising:

a display device comprising a multiplicity of pixels displaying an ultrasound image of a blood vessel with a graphic representing a range gate and a graphic representing a vessel slope overlying said blood vessel; and a computer programmed to perform the steps of:
    determining the position of a first boundary of said blood vessel; and
    controlling said display device to adjust the position of said range gate if the change in the position of the boundary relative to said range gate is equal to or greater than a predetermined threshold.

21. The system as recited in claim 20, wherein said position determining step comprises the step of determining the address of a pixel on said first boundary.

22. The system as recited in claim 21, wherein said pixel on said first boundary is located along a line generally perpendicular to said vessel slope graphic.

23. The system as recited in claim 20, wherein said computer is further programmed to perform the step of determining the position of a second boundary of said blood vessel, said controlling step comprising the step of adjusting the position of said range gate relative to said first and second boundaries.

24. The system as recited in claim 23, wherein said pixels on said first and second boundaries are located along a line generally perpendicular to said vessel slope graphic.

25. A method of operating a computerized ultrasound imaging system, comprising the steps of:

searching along a line for a point on a boundary of a moving blood vessel in accordance with a search algorithm;

determining a location of said point on said boundary; and automatically adjusting the position of a range gate to track said moving blood vessel, said adjustment being a function of at least said location of said point on said boundary.

26. The method as recited in claim 25, wherein said searching step comprises the steps of searching from a center point and storing a point as an edge point if it is the first of a plurality of points displaying B-mode intensity data instead of color flow velocity data.

27. The method as recited in claim 25, wherein said searching step comprises the steps of searching from a center point and storing a point as an edge point if it is the first of a plurality of points displaying B-mode intensity data instead of color flow power data.

28. The method as recited in claim 25, wherein said searching step comprises the steps of searching from a center point along a line by replacing each B-mode intensity value by an average of itself and its two neighbors, and storing a point as an edge point if a difference between a peak B-mode intensity value and a minimum B-mode intensity value along the averaged line exceeds a threshold.

29. A computerized ultrasound imaging system programmed to search along a line for a point on a boundary of a moving blood vessel in accordance with a search algorithm, determine a location of said point on said boundary, and automatically adjust the position of a range gate to track said moving blood vessel, said adjustment being a function of at least said location of said point on said boundary.

30. The system as recited in claim 29, wherein said searching step comprises the steps of searching from a center point and storing a point as an edge point if it is the first of a plurality of points displaying B-mode intensity data instead of color flow velocity data.

31. The system as recited in claim 29, wherein said searching step comprises the steps of searching from a center point and storing a point as an edge point if it is the first of a plurality of points displaying B-mode intensity data instead of color flow power data.

32. The system as recited in claim 29, wherein said searching step comprises the steps of searching from a center point along a line by replacing each B-mode intensity value by an average of itself and its two neighbors, and storing a point as an edge point if a difference between a peak B-mode intensity value and a minimum B-mode intensity value along the averaged line exceeds a threshold.

* * * * *